US009291556B2

(12) United States Patent
Nakagawa et al.

(10) Patent No.: US 9,291,556 B2
(45) Date of Patent: Mar. 22, 2016

(54) OBJECTIVE OPTICAL SYSTEM FOR ATR MEASUREMENT, AND ATR MEASUREMENT DEVICE

(75) Inventors: Takao Nakagawa, Tokyo (JP); Koji Masutani, Tokyo (JP); Tetsuya Sugimoto, Tokyo (JP)

(73) Assignee: S.T. Japan, Inc., Tokyo (JP)

( * ) Notice: Subject to any disclaimer, the term of this patent is extended or adjusted under 35 U.S.C. 154(b) by 0 days.

(21) Appl. No.: 14/378,933

(22) PCT Filed: Apr. 20, 2012

(86) PCT No.: PCT/JP2012/002745
§ 371 (c)(1),
(2), (4) Date: Dec. 15, 2014

(87) PCT Pub. No.: WO2013/124909
PCT Pub. Date: Aug. 29, 2013

(65) Prior Publication Data
US 2015/0131083 A1    May 14, 2015

(30) Foreign Application Priority Data

Feb. 22, 2012    (JP) ................................ 2012-036152

(51) Int. Cl.
| G01J 3/00 | (2006.01) |
| G01N 21/552 | (2014.01) |
| G01N 21/27 | (2006.01) |
| G02B 19/00 | (2006.01) |
| G02B 21/02 | (2006.01) |
| G02B 21/04 | (2006.01) |

(52) U.S. Cl.
CPC .............. *G01N 21/552* (2013.01); *G01N 21/27* (2013.01); *G02B 19/009* (2013.01); *G02B 19/0028* (2013.01); *G02B 19/0085* (2013.01); *G02B 21/02* (2013.01); *G02B 21/04* (2013.01); *G01N 2201/062* (2013.01); *G01N 2201/08* (2013.01)

(58) Field of Classification Search
CPC .......................................................... G01J 3/00
USPC .............................................................. 356/51
See application file for complete search history.

(56) References Cited

U.S. PATENT DOCUMENTS

| 5,093,580 | A | 3/1992 | Sting | |
| 5,313,264 | A * | 5/1994 | Ivarsson | G01N 21/552 250/458.1 |
| 5,859,727 | A | 1/1999 | Tsuchiya | |
| 6,907,390 | B1 | 6/2005 | Reffner | |

FOREIGN PATENT DOCUMENTS

| JP | H04138340 A | 5/1992 |
| JP | H06034528 A | 2/1994 |
| JP | H1096861 A | 4/1998 |
| JP | H10185805 A | 7/1998 |
| JP | 2002532726 A | 10/2002 |

* cited by examiner

*Primary Examiner* — Roy M Punnoose
(74) *Attorney, Agent, or Firm* — Miller Law Group, PLLC

(57) ABSTRACT

An objective optical system for ATR measurement is provided with a housing, in the interior, an ATR crystal that is transparent in visible light and has a semispherical surface through which light enters; an infrared optical member for irradiating a sample with infrared light at an angle that is equal to or greater than the critical angle; a visible light irradiation optical member which is disposed in the interior of the casing and which irradiates the sample with visible light from an angle less than the critical angle; and an observation optical member which is disposed on a position that is offset from the reflection angle relative to the angle at which the visible light enters the sample and which guides the scattering light from the sample to an observation device. As a consequence, it is possible to clearly observe the position of a sample subjected to ATR measurement.

6 Claims, 4 Drawing Sheets

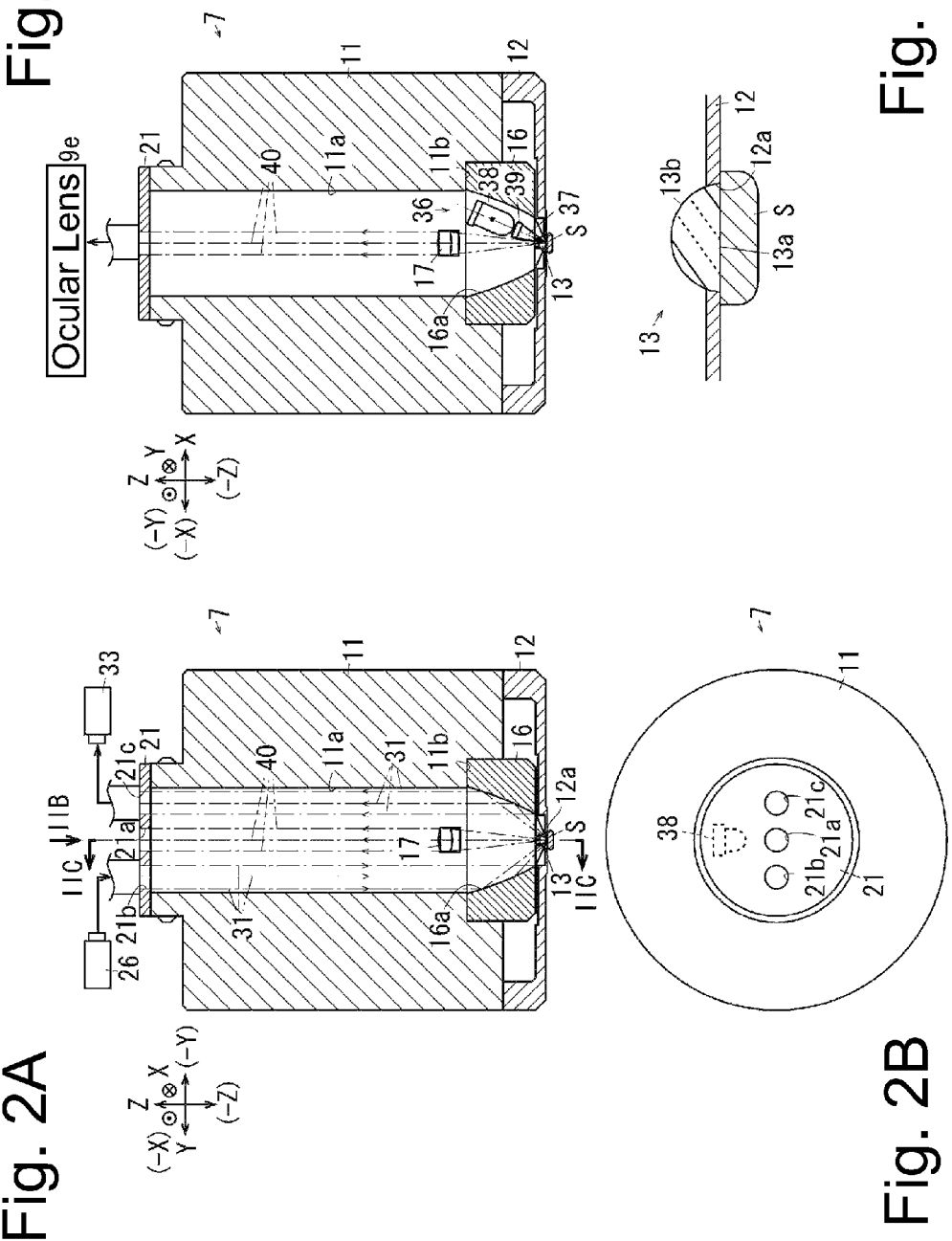

OBJECTIVE OPTICAL SYSTEM FOR ATR MEASUREMENT, AND ATR MEASUREMENT DEVICE

FIELD OF THE INVENTION

The present invention relates to an objective optical system for ATR (Attenuated Total Reflectance) measurement, which adopts ATR crystals that are transparent to visible light, and an ATR measurement instrument, in particular, the present invention relates to an objective optical system for ATR measurement and an ATR measurement instrument, with which a sample can be observed visually. In addition, in the specification and claims, the optical system comprises lens and reflectors.

BACKGROUND OF THE INVENTION

In the past, to carry out spectrophotometric determination on samples that are not transparent to light, the following ATR (Attenuated Total Reflectance) measurement was performed: the totally reflecting surface of a crystal, which has a high index of refraction, is attached closely to a sample, and light is irradiated on the ATR crystal at an incident angle greater than the critical angle (total reflection angle), so that the light is totally reflected, and an evanescent wave generated on the surface of the ATR crystal infiltrates into the sample; in that way, the properties of the sample are measured. When carrying out the ATR measurement, if the measured position of the sample can't be ascertained by observation, the specific position where the ATR measurement is performed will be unknown. Therefore, a mechanism with which the measured position of the sample can be observed and set is required.

Among ATR measurement techniques, the techniques for observing and setting the measured positions of a sample, as described in U.S. Pat. No. 5,093,580, issued on Mar. 3, 1992, to Donald W. Sting, particularly at column 3, line 43, to column 4, line 31, and at column 7, line 63 to column 8, line 29, with reference being made to FIG. 1; and as described in Japanese Patent Publication No. JP1994-34529, at paragraphs 0010-0011, with reference being made to FIG. 1, are known.

The following technique is described in U.S. Pat. No. 5,093,580: a visible light source (2) and a radiant energy source (3) can be switched by switching a switch mirror (6), to irradiate the sample with visible light (4) or radiant energy light (8), and the visual image can be confirmed through a viewing port (13), or an ATR measurement can be carried out with a detector (25). In the technique described in the patent document 1, the following structure is formed: visible light (4) and radiant energy light (8) are irradiated through a common light path and common optical systems (20, 21) to an ATR crystal (22) and a sample (26).

The following technique is described in Japanese Patent Publication No. JP1994-34528: illumination light (8) for ATR measurement is irradiated on an ATR crystal (1) at an incident angle greater than the critical angle, the reflected light is reflected by a Cassegrain objective optical system (2) and is detected by an optical detector (5), meanwhile illumination light (7) for observation is irradiated at an incident angle that is smaller than the critical angle and meets regular reflection criteria, and the reflected light is reflected by a Cassegrain objective optical system (2) and detected by an ocular lens (6).

In the past ATR measurements, to ascertain the measured positions of a sample, a camera for shooting pictures must be provided at the same side as infrared light irradiation; however, when shooting with the camera, a visible light source that can emit an appropriate quantity of light is required (for illumination). Here, under case that the sample and the ATR crystal are transparent to visible light, the camera can be used for shooting, provided that an illumination light source is arranged at the fixture side where the sample is pressed against the ATR crystal. However, under case that the sample is non-transparent to visible light, such as the structures described in U.S. Pat. No. 5,093,580 and JP1994-34528, illumination is required at the camera side.

However, in the technique described in U.S. Pat. No. 5,093,580, since the visible light and the ATR measuring light pass through a common light path, the visible light (illumination light) will also be totally reflected, resulting in the following problem: there is nearly no light scattered from the sample, only illumination light that contains nearly no sample information comes to the observer side (e.g., the camera), and nearly no image of the sample can be observed in the observed image.

In the technique described in JP1994-34528, since the illumination light (7) for observation irradiates at an angle that meets the regular reflection criteria, the light that is regularly reflected from the surface of the ATR crystal forms strong background light and superposes the observed image; therefore, it is difficult to judge in the image.

In view of the above problems, the technical task of the present invention is to provide a technical solution, with which the measured positions of a sample in an ATR measurement can be observed clearly.

SUMMARY OF THE INVENTION

To fulfill the above technical task, the objective optical system for ATR measurement as described in claim 1 comprises:

an ATR crystal, which is transparent to visible light, and has a totally reflecting surface that contacts with a sample and a hemispheric surface for light incidence;

a casing, which has a space formed in it for the infrared light that is irradiated on the ATR crystal to pass through, and accommodates the ATR crystal;

an optical component for infrared light irradiation, which is supported on the casing and irradiates infrared light on the sample at an incident angle greater than the critical angle determined according to the refraction angle of the ATR crystal and the sample, and guides the reflected light from the sample which has been irradiated by the infrared light into a detector;

an optical component for visible light irradiation, which is arranged in the casing, and irradiates visible light on the sample at an angle smaller than the critical angle;

an optical component for observation, which is arranged at a position staggered from the reflection angle associated to the incident angle of visible light irradiated to the sample, and guides scattered light from the sample which has been irradiated by visible light into an observation unit.

The invention described in claim 2 relates to the objective optical system for ATR measurement as described in claim 1, and comprises a visible light source that emits visible light and a light condensing component that condenses the visible light from the visible light source.

The invention described in claim 3 relates to the objective optical system for ATR measurement as described in claim 1, and comprises a visible light source that emits visible light and an optical fiber that guides the visible light from the visible light source to the sample.

To solve the above technical problem, the invention described in claim 4 relates to an ATR measurement instrument, comprising:

the objective optical system as described in any one of the claims 1-3;

a detector, which detects infrared light outputted from the objective optical system;

an observation unit, which receives visible light outputted from the objective optical system, so that an image can be observed.

Compared with conventional systems that don't have the optical component disclosed in the present invention, the system described in claim 1 and claim 4 enables the user to observe the measured positions of a sample clearly when carrying out ATR measurement.

Compared with conventional systems in which the visible light source is arranged outside of the casing, the system described in claim 2 and 3 has a smaller overall structure.

BRIEF DESCRIPTION OF THE DRAWINGS

FIG. 2A is a schematic cross-sectional view of a first embodiment of the main part of an objective optical system for ATR measurement;

FIG. 2B is a top view of the structure depicted in FIG. 2A when viewed from the direction of the arrow IIB;

FIG. 2C is a cross-sectional view taken along the line IIC-IIC in FIG. 2A; and;

FIG. 2D is an enlarged view of the main part depicted in FIG. 2A;

DETAILED DESCRIPTION OF THE PREFERRED EMBODIMENTS

Figure 1:
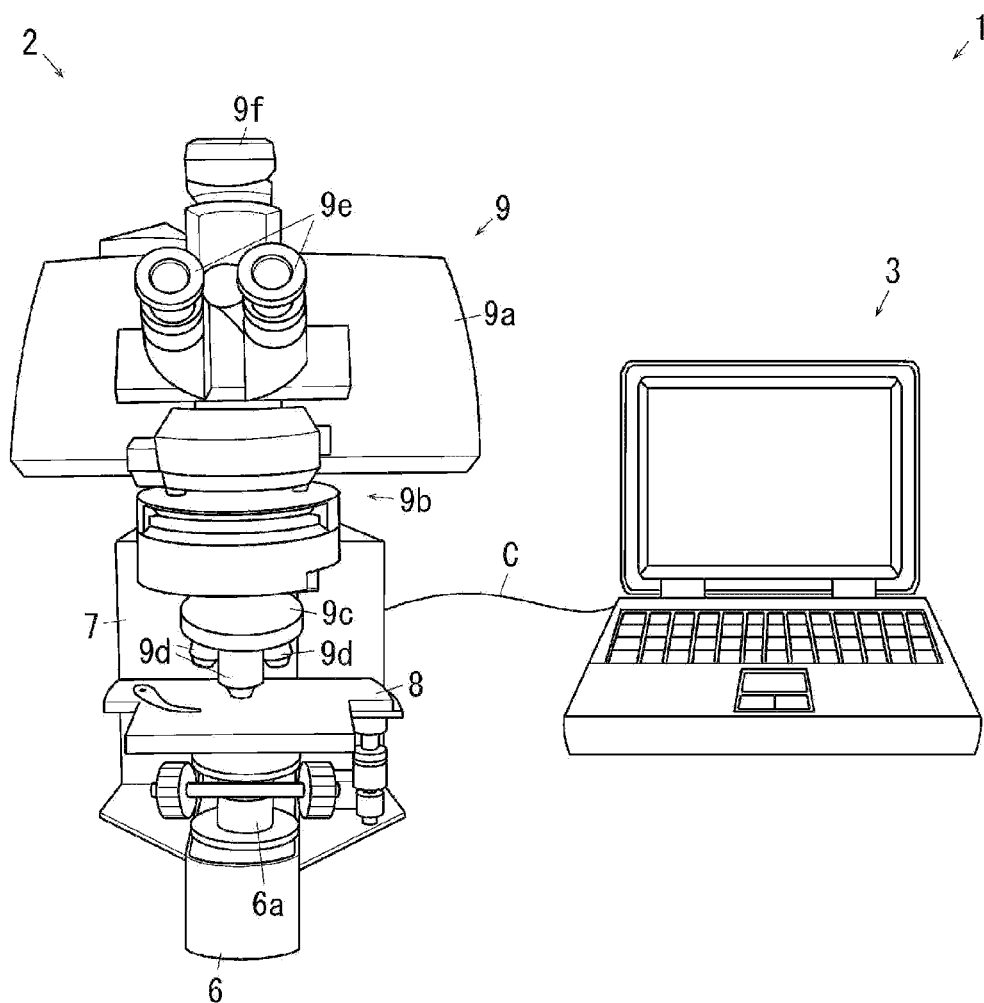
FIG. 1 is a schematic diagram of the ATR measurement instrument in embodiment 1.

Hereunder some exemplary embodiments (the embodiments below) of the present invention will be described with reference to the accompanying drawings; however, the present invention is not limited to these embodiments.

In addition, to facilitate understanding of the following content, in the accompanying drawings, the front-back direction (the direction perpendicular to the paper plane) is defined as X direction, the left-right direction is defined as Y direction, and the up-down direction is defined as Z direction; the direction or side indicated by an arrow X, –X, Y, –Y, Z, or –Z is front, back, right, left, up, or down, or front side, back side, right side, left side, upside, or downside.

Moreover, in the drawings, a symbol "○" with a "•" in it refers to an arrow that points from the inner side of the paper towards the outer side of the paper, while a symbol "○" with a "×" in it refers to an arrow that points from the outer side of the paper towards the inner side of the paper.

Furthermore, in the following content described with reference to the accompanying drawings, the graphic representation of other components except for the components required for the description is omitted appropriately, for clarity purpose.

Embodiment 1

FIG. 1 is a schematic diagram of the ATR measurement instrument in the first embodiment.

As shown in FIG. 1, the ATR measurement instrument 1 in embodiment 1 of the present invention comprises a device body 2, and, as an example of a processor, a notebook computer 3, wherein, the notebook computer 3 is connected with the device body 2 through a connection cable C, to process the data from the device body 2.

The device body 2 comprises a mirror base part 6 on the bottom, and a mirror post part 7 that extends upwards from the mirror base part 6. An illumination part 6a is supported on the top surface of the mirror base part 6, and the illumination part 6a outputs illumination light for observation of the sample. A stage 8 is supported on the bottom of the mirror post part 7 in a way that the stage 8 can ascend/descend above the illumination part 6a in up-down direction, and the stage 8 supports a sample on its top surface. On the top of the mirror post part 7, as an example of measuring part, a FT-IR part 9 is supported.

The FT-IR part 9 comprises a main body part 9a in it; an infrared light source and an infrared light detection part are arranged in the main body part 9a. A connecting part 9b is connected on the main body part 9a, and the connecting part 9b has a space or optical system (not shown) through which the infrared light from the infrared light source to the sample and the reflected and scattered infrared light pass, where the reflected and scattered infrared light is produced when the infrared light from the infrared light source irradiates the sample. A revolver 9c is supported in a rotatable manner on the bottom of the connecting part 9b above the stage 8, and a plurality of objective optical systems 9d are supported on the revolver 9c. In addition, an ocular lens 9e is supported on the top of the connecting part 9b, and the ocular lens 9e is an example of an observation part for users to observe the sample S visually.

In addition, such a measurement instrument is known in the art, for example, an IlluminateIR unit from Smiths Detection can be used.

FIG. 2A-D is a schematic diagram of the objective optical system for ATR measurement in embodiment 1, wherein, FIG. 2A is a sectional view of the main part, FIG. 2B is a view of the structure when viewed from the direction of the arrow IIB in FIG. 2A, FIG. 2C is a sectional view along the line IIC-IIC in FIG. 2A, and FIG. 2D is an enlarged view of the main part in FIG. 2A.

As shown in FIG. 2A-D, the objective optical system 9d in embodiment 1 comprises, as an example of the main body of the optical system, a cylindrical casing body 11 that extends in up-down direction. A through-hole 11a in up-down direction is formed in the middle part of the casing body 11, and a space for light to pass is formed in the through-hole 11a. On the bottom of the through-hole 11a, as an example of a supporting part of the optical component, a recessed supporting part 11b for the infrared objective optical system is formed.

A crystal supporting component 12 is supported on the bottom of the casing body 11, and a crystallization opening 12a for crystallizing that runs through the up-down direction is formed in the middle part of the crystal supporting component 12.

An ATR crystal 13 is fixedly supported at inner side (on the side surface) of the crystal exposure opening 12a. In FIG. 2D, the ATR crystal 13 in embodiment 1 is in a hemispheric shape, comprising a flat or slightly recessed convex totally reflecting surface 13a that contacts with the sample S on the bottom and a hemispheric surface 13b for light incidence on the top. In addition, the ATR crystal 13 in embodiment 1 is formed by a diamond ATR crystal that is transparent to visible light and infrared light.

In the recessed supporting part 11b above the ATR crystal 13, as an example of an optical component for infrared light, an infrared objective optical system 16 is supported. On the inner surface of the infrared objective optical system 16, a reflecting surface 16a is formed, which is in doughnut shape or annular shape when viewed from top. The reflecting surface 16a in embodiment 1 is in a parabolic shape, with the focal point position of the reflecting surface 16a corresponding to the position of the sample S, i.e., the position of the totally reflecting surface 13a of the ATR crystal 13. In addition, the reflecting surface 16a is not limited to parabolic shape, which is to say, it can utilizes a known optical system in the prior art, for example, it can be a combination of an elliptical surface and a condensing lens, or a Cassegrain optical unit.

On the bottom of the through-hole 11a, as an example of an optical component for observation, an observation lens 17 is supported at the center of the through-hole 11a. The focal point position of the observation lens 17 in embodiment 1 corresponds to the position of the sample S.

In FIG. 2A, on the top end of the through-hole 11a, as an example of a light path-separating plate, a circular plate shaped connecting part 21 is supported. In the middle part of the connecting part 21, an output port 21a for observation that runs through the up-down direction is arranged; at the left side of the output port 21a, an infrared light input port 21b is arranged; at the side opposite to the input port 21b, an infrared light output port 21c is formed, with the output port 21a held between the infrared light input port 21b and the infrared light output port 21c. The casing body 11, crystal supporting component 12, and connecting part 21 constitute a casing 11+12+21 in embodiment 1.

The output port 21a for observation is connected via the connecting part 9b to the ocular lens 9e in a way that the user can observe through the ocular lens 9e. Alternatively, not limited to the ocular lens 9e, the following structure can be formed, wherein, for example, a three-port unit can be equipped with, as an example of an observation unit that can take visual images, a CCD camera 9f, which takes images of the light output from the output port 21a, and then the images can be displayed on the monitor of the notebook computer 3.

In addition, in the infrared light input port 21b, infrared light 31 from an infrared light source 26 supported in the main body part 9a of the FT-IR part 9 is inputted through the connecting part 9b. Then, the infrared light 31 is guided from the input port 21b into the through-hole 11a, and irradiates to the ATR crystal 13 after being reflected and condensed by the objective optical system 16. Moreover, in embodiment 1, the positions of the reflecting surface 16a and input port 21b of the infrared objective optical system 16 are arranged in a way that the infrared light 31 is irradiated to the ATR crystal 13 at an angle greater than the critical angle.

On the output port 21c of the infrared light, a detector 33 is connected via the connecting part 9b, and the detector 33 is supported in the main body part 9a of the FT-IR part 9 and designed to detect infrared light. Therefore the infrared light 31 is totally reflected from the sample S and ATR crystal 13 and runs through the infrared objective optical system 16, is outputted from the output port 21c, and detected by the detector 33; the detected data is transmitted to the notebook computer 3, where the data is processed and displayed.

In FIG. 2C, at an upper diagonal position in front of the ATR crystal 13, as an example of an optical component for visible light irradiation, an illuminator 36 is arranged. The illuminator 36 in embodiment 1 comprises, as an example of a visible light source that emits visible light (illumination light) 37, a Light Emitting Diode (LED) 38, and, as a condensing part that condenses the illumination light 37 from the LED 38 on the sample S, a lens 39. Moreover, the LED 38 in embodiment 1 is arranged in an inclined state in relation to the axial direction (i.e., up-down direction) of the through-hole 11a.

In addition, in embodiment 1, the position of the illuminator 36 is arranged in the following way: the light axis of the illumination light 37 condensed by the lens 39 is irradiated to the sample S at an incident angle smaller than the critical angle determined on the basis of the indexes of refraction of the ATR crystal 13 and sample S, at the same time, the light axis is staggered (inclined) from the light axis of the viewing optical system 17 in relation to the reflection angle associated to the incident angle.

Therefore, the system is formed in the following way: the regularly reflected light of the illumination light 37 from the hemispheric surface 13b of the ATR crystal 13 or the boundary surface 13a of the sample doesn't enter into the viewing optical system 17 directly; instead, only the scattered light 40 reflected from the sample enters into the viewing optical system 17. In addition, it can be seen from FIG. 2A and FIG. 2C: in embodiment 1, the light path of the infrared light 31 and the light path of the illumination light 37 are arranged in a 90° cross manner when viewed from top, and the LED 38 and lens 39 are arranged at positions where they don't obstruct the infrared light 31.

(Effects of Embodiment 1)

Figure 3A:
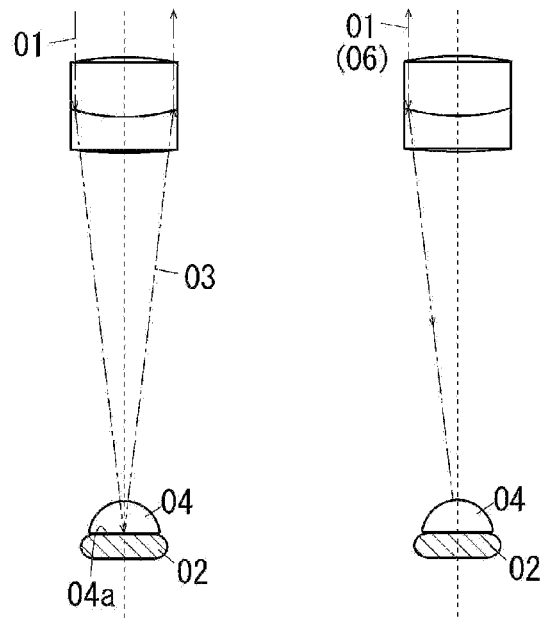
FIG. 3A is a schematic diagram of the regular reflection of the illumination light path of a built-in epi-illumination in the prior art from the surface at the sample side of the ATR crystal.
Figure 3B:
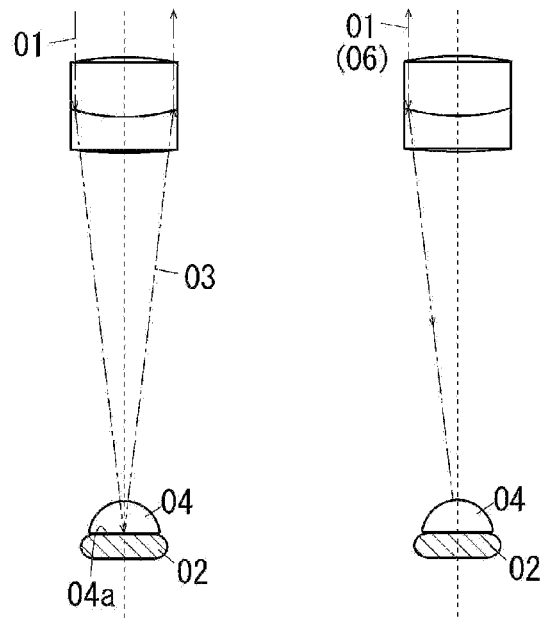
FIG. 3B is a schematic diagram similar to that of FIG. 3A, but of regular reflection of the illumination light from the surface at the incidence side of the ATR crystal.

FIG. 3A-B is a schematic diagram of the light path of built-in epi-illumination in the prior art, wherein, FIG. 3A is a schematic diagram of regular reflection of the illumination light from the surface at the sample side of the ATR crystal, and FIG. 3B is a schematic diagram of regular reflection of the illumination light from the surface at the incidence side of the ATR crystal.

In the ATR measurement instrument 1 with the above-mentioned structure in embodiment 1, the sample S is observed through the ocular lens 9e and infrared spectral photometry (ATR measurement) is carried out in the FT-IR part 9 when the stage 8 is controlled to ascend/descend and the sample S on the stage 8 is pressed against the ATR crystal 13.

Here, when measuring a sample S which is transparent to the measuring light, a bright image will be obtained in the visual field through the ocular lens 9e, since the light from the illumination part 6a passes through the sample S and ATR crystal 13. In addition, in the ATR measurement instrument 1 in embodiment 1, when a sample S that is non-transparent to the measuring light is measured, the illumination light 37 from the LED 38 will be scattered and reflected from the sample S, and the scattered light 40 will pass through the optical system 17; thus, a dark-field image could be observed in the visual field through the ocular lens 9e. In that case, the regular reflection angle of the illumination light 37 from the LED 38 is staggered from the position of the viewing optical system 17, and the regularly reflected light of the illumination light 37 will hardly reach to the ocular lens 9e.

In FIG. 3A-B, for example, irradiating illumination light 01 (dark-field or epi-illumination) through the viewing output port 21a (in FIG. 2) can be considered; however, in such a structure, the reflected light contains little information of the sample 02, since the light 03 regularly reflected at the boundary surface 04a of the sample 02 is strongly reflected from the surface of the ATR crystal 04, similar to the case shown in FIG. 3A. In addition, as shown in FIG. 3B, the reflected light 06 of the illumination light 01 reflected from the incident surface of the ATR crystal 04 doesn't contain all information of the sample 02. Since they superpose as strong background light in the visual field of the sample, the image of signal light that is scattered and reflected from the sample 02 and contains the information of the sample 02 will be hidden in the strong background light, and difficult to observe.

In addition, with the structure described in the patent document 1, in the case that the light for observation is irradiated at an incident angle that meets total reflection criteria, or, with the structure described in the patent document 2, in the case that the light for observation is irradiated at an incident angle that meets regular reflection criteria, since almost all of the former and the majority of the latter is the light reflected from the boundary surface 04a of the ATR crystal 04, they function as background light. Thus, it is difficult to discriminate the image of signal light that contains the information of the sample 02. Moreover, in the case that the ATR crystal is in a plate shape and the side through which the illumination light passes is a flat surface, the adverse effect of background light can be inhibited, since the light reflected from the surface of the ATR crystal at the incident side doesn't form an image in the CCD camera 9f; however, in this case, the image will be blur and potential problems of the sample can't be identified correctly, owing to the effect of aberration of the plate.

In contrast, in the ATR measurement instrument 1 in embodiment 1, there is nearly no background light, since the regularly reflected light can hardly reach to the ocular lens 9e; therefore, compared with the image obtained with the existing structure in the prior art, the image obtained in the ATR measurement instrument 1 is sharp and clear. Thus, the position of the measured object in the ATR measurement can be ascertained by observing the sharp and clear image, and the user can adjust the intended measured position of the sample S while observing the sharp and clear image. In addition, infrared light 31 can be irradiated in relation to the measured position of sample S preset by the user, and ATR measurement can be carried out accordingly.

Moreover, in the objective optical system 9d for ATR measurement in embodiment 1, the illuminator 36 and viewing optical system 17 can be built in the objective optical system 9d, so that they form an integral assembly, to attain a purpose of miniaturization; furthermore, the objective optical system 9d, including the illuminator 36, can be replaced as an integral replaceable unit.

Embodiment 2

Figure 4:
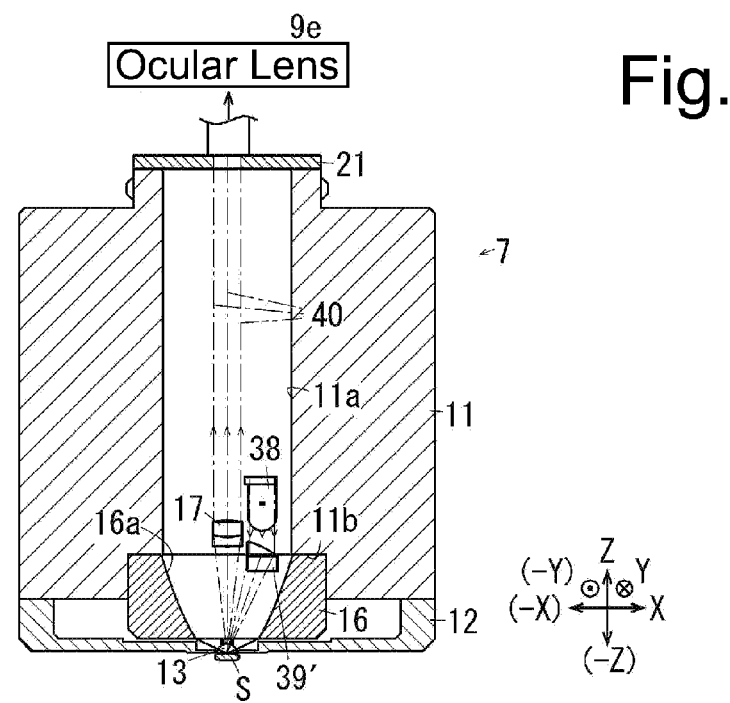
FIG. 4 is a schematic diagram of the objective optical system for ATR measurement in a second embodiment of the invention, corresponding to FIG. 2C.

FIG. 4 is a schematic diagram of the objective optical system for ATR measurement in a second embodiment of the invention, corresponding to FIG. 2C of embodiment 1.

Hereunder an embodiment 2 of the present invention will be described. In the description of embodiment 2, the constituent elements that correspond to the constituent elements in embodiment 1 are denoted with the same symbols, and the description related to them will be omitted. In embodiment 2, the following aspect is different from embodiment 1, while other aspects are the same as embodiment 1.

As shown in FIG. 4, in the objective optical system 9d for ATR measurement in embodiment 2, different from the case in embodiment 1, the LED 38 is arranged downwards; below the LED 38, a lens 39' is arranged, as an example of a light condensing component. The lens 39' in embodiment 2 is constituted by a part of a plano-convex lens with the focal point set at the sample S; however, the lens 39' is not limited to that, for example, it can be a Fresnel lens, etc. The LED 38 and lens 39' constitute the illuminator 36 in embodiment 2.

(Effects of Embodiment 2)

In the objective optical system 9d for ATR measurement with the above-mentioned structure in embodiment 2, the measured position of the sample in ATR measurement can be ascertained by observing a sharp and clear image, similar to the case of the objective optical system 9d in embodiment 1.

Embodiment 3

Figure 5:
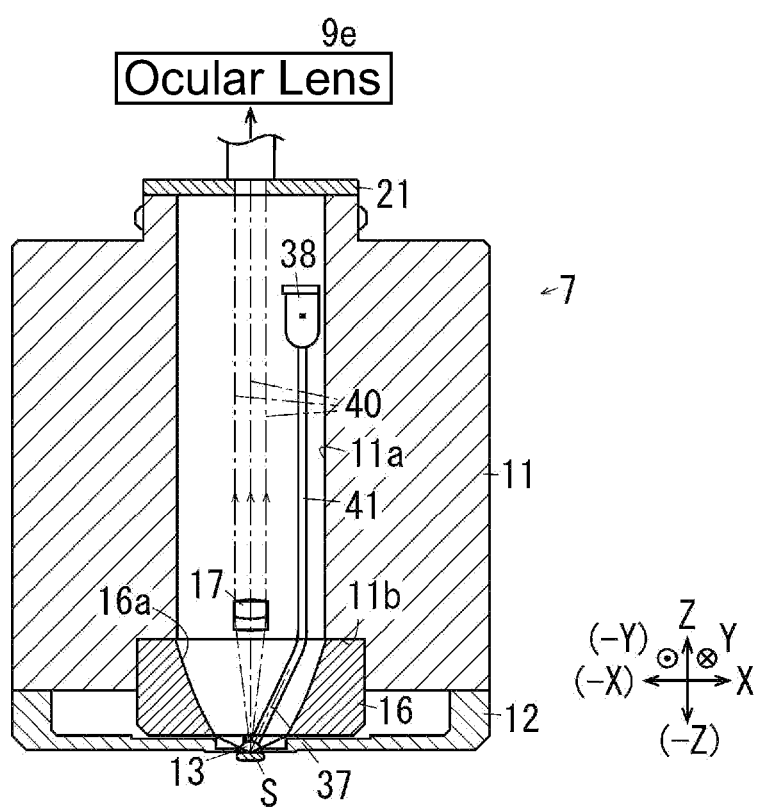
FIG. 5 is a schematic diagram of the objective optical system for ATR measurement in a third embodiment of the invention, corresponding to FIG. 2C.

FIG. 5 is a schematic diagram of the objective optical system for ATR measurement in a third embodiment of the invention, corresponding to FIG. 2C of embodiment 1.

Hereunder an embodiment 3 of the present invention will be described. In the description of embodiment 3, the constituent elements that correspond to the constituent elements in embodiment 1 are denoted with the same symbols, and the description related to them will be omitted. In embodiment 3, the following aspect is different from embodiment 1, while other aspects are the same as embodiment 1.

As shown in FIG. 5, in the objective optical system 9d for ATR measurement in embodiment 3, different from the case in embodiment 1, the LED 38 is arranged on the top of the through-hole 11a; in addition, in the through-hole 11a, an optical fiber 41 is arranged, extending from the LED 38 to the ATR crystal 13. The top end of the optical fiber 41 is arranged near the LED 38, while the bottom end of the optical fiber 41 is arranged near the hemispheric surface 13b of the ATR crystal 13. In addition, the center at the ATR crystal side of the optical fiber 41, i.e., the light axis of the illumination light 37 that are arranged to the center of the ATR crystal in the same way as in the case in embodiment 1. The LED 38 and the optical fiber 41 constitute the illuminator 36 in embodiment 3.

(Effects of Embodiment 3)

In the objective optical system 9d for ATR measurement with the above-mentioned structure in embodiment 3, the measured position of the sample S in ATR measurement can be ascertained by observing a sharp and clear image, similar to the case of the objective optical system 9d in embodiment 1.

(Variants)

Though the present invention is described above in some embodiments, the present invention is not limited to the embodiments. A variety of variations can be made within the essential scope of the present invention as defined in the claims. Hereunder some variants (H01)-(H04) will be described.

(H01) The structure of the device body 2 is not limited to the embodiments described above. It can be in any known form in the prior art, for example, the objective optical system 9d can be in a reversed structure in up-down direction, and the structure of the pressurizing fixture 8 can be altered appropriately. In addition, an attachment structure that can accommodate known liquid samples or gas samples in the prior art can be formed.

(H02) Though the light source of the illuminator 36 is a LED in the above embodiments, it is not limited to that; for example, an organic EL or any light source can be used.

(H03) In above embodiment 3, preferably the LED 38 is built in the objective optical system 9d; however, alternatively, the LED 38 can be arranged outside of the objective optical system 9d. In addition, before the light is shot into the optical fiber 41, it can be condensed through a lens, for example.

(H04) In above embodiments, the optical components 16, 17, and 36 are composed of one component respectively; however, the present invention is not limited to that. For example, the optical components can be formed by a plurality of lenses, reflectors, optical fibers, or other optical components in any combination.

It will be understood that changes in the details, materials, steps and arrangements of parts which have been described and illustrated to explain the nature of the invention will occur to and may be made by those skilled in the art upon a reading of this disclosure within the principles and scope of the invention. The foregoing description illustrates the preferred embodiments of the invention; however, concepts, as based upon the description, may be employed in other embodiments without departing from the scope of the invention. The invention is not otherwise limited, except for the recitation of the claims set forth below.

The invention claimed is:

1. An objective optical system for ATR measurement, comprising:
   an ATR crystal, which is transparent to visible light, and has a totally reflecting surface that contacts with a sample and a hemispheric surface for light incidence;
   a casing, which has a space formed in it for the infrared light that is irradiated on the ATR crystal to pass through, and accommodates the ATR crystal;
   an optical component for infrared light irradiation, which is supported on the casing and irradiates infrared light on the sample at an incident angle greater than the critical angle determined according to the refraction angle of the ATR crystal and the sample, and guides the reflected light from the sample which has been irradiated by the infrared light into a detector;
   an optical component for visible light irradiation, which is arranged in the casing, and irradiates visible light on the sample at an angle smaller than the critical angle;
   an optical component for observation, which is arranged at a position staggered from the reflection angle associated to the incident angle of visible light irradiated to the sample, and guides scattered light from the sample which has been irradiated by visible light into an observation unit.

2. The objective optical system for ATR measurement according to claim 1, comprising a visible light source that emits visible light and a light condensing component that condenses the visible light from the visible light source.

3. The objective optical system for ATR measurement according to claim 1, comprising a visible light source that emits visible light and an optical fiber that guides the visible light from the visible light source to the sample.

4. An ATR measurement instrument, comprising:
   an ATR crystal, which is transparent to visible light, and has a totally reflecting surface that contacts with a sample and a hemispheric surface for light incidence;
   a casing, which has a space formed in it for the infrared light that is irradiated on the ATR crystal to pass through, and accommodates the ATR crystal;
   an optical component for infrared light irradiation, which is supported on the casing and irradiates infrared light on the sample at an incident angle greater than the critical angle determined according to the refraction angle of the ATR crystal and the sample, and guides the reflected light from the sample which has been irradiated by the infrared light into a detector;
   an optical component for visible light irradiation, which is arranged in the casing, and irradiates visible light on the sample at an angle smaller than the critical angle;
   an optical component for observation, which is arranged at a position staggered from the reflection angle associated to the incident angle of visible light irradiated to the sample, and guides scattered light from the sample which has been irradiated by visible light into an observation unit;
   a detector, which detects infrared light outputted from the objective optical system; and
   an observation unit, which receives visible light outputted from the objective optical system, so that an image can be observed.

5. The ATR measurement instrument according to claim 4, comprising a visible light source that emits visible light and a light condensing component that condenses the visible light from the visible light source.

6. The ATR measurement instrument according to claim 4, comprising a visible light source that emits visible light and an optical fiber that guides the visible light from the visible light source to the sample.

* * * * *